United States Patent [19]
Vidal et al.

[11] Patent Number: 5,334,216
[45] Date of Patent: Aug. 2, 1994

[54] HEMOSTATIC PLUG

[75] Inventors: Claude A. Vidal, Santa Barbara; Russel J. Redmond, Goleta, both of Calif.; Joshua Makower, Nanuet, N.Y.

[73] Assignee: Howmedica Inc., New York, N.Y.

[21] Appl. No.: 988,567

[22] Filed: Dec. 10, 1992

[51] Int. Cl.$^5$ .............................. A61B 17/00
[52] U.S. Cl. ............................ 606/213; 606/1; 606/151
[58] Field of Search ..................... 606/151–156, 606/191, 198, 213.1; 128/887, 899; 604/904; 623/1, 11, 12; 600/32

[56] References Cited

U.S. PATENT DOCUMENTS

| | | | |
|---|---|---|---|
| 2,127,903 | 8/1938 | Bowen | 606/154 |
| 3,463,158 | 8/1969 | Schmitt et al. | 606/155 |
| 4,217,664 | 8/1980 | Faso | 606/156 |
| 4,483,339 | 11/1984 | Gillis | 606/156 |
| 4,661,101 | 4/1987 | Sustmann | 604/904 |
| 4,778,467 | 10/1988 | Stensaas | 606/152 |
| 4,863,668 | 9/1989 | Griffiths et al. | 606/152 |
| 4,986,831 | 1/1991 | King et al. | 606/151 |
| 5,059,211 | 10/1991 | Stack et al. | 606/198 |
| 5,116,357 | 5/1992 | Eberbach | 606/213 |
| 5,171,262 | 12/1992 | MacGregor | 623/12 |
| 5,192,300 | 3/1993 | Fowler . | |
| 5,192,302 | 3/1993 | Kensey et al. . | |

FOREIGN PATENT DOCUMENTS 0482350 4/1992 European Pat. Off. .
WO/9222252 12/1992 PCT Int'l Appl. .

Primary Examiner—Stephen C. Pellegrino
Assistant Examiner—Jeffrey A. Schmidt
Attorney, Agent, or Firm—Haugen and Nikolai

[57] ABSTRACT

A method of making a hemostatic plug for placement at a site where hemostatic treatment is indicated. The method comprises rolling a sheet of a hemostatic material a plurality of turns onto a generally cylindrical forming tool to thereby produce a rolled hemostatic plug having an opening therethrough along its longitudinal axis. In addition to employing one sheet of hemostatic material having a single density to form a plug, two sheets of hemostatic material having different densities can be rolled in tandem to each other on the forming tool, with one sheet overlapping an exposed wedge portion of the other sheet. The plugs thus formed can be longitudinally compressed if subsequent longitudinal expansion is desired. A typical placement site for which the plug is preferably employed is a puncture wound wherein an entry penetration of an artery and a tissue channel leading thereto are present.

11 Claims, 6 Drawing Sheets

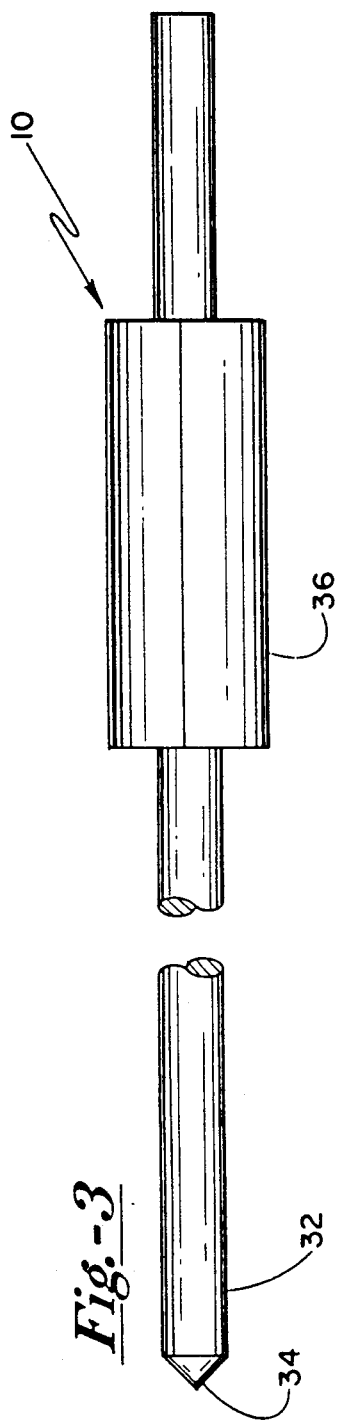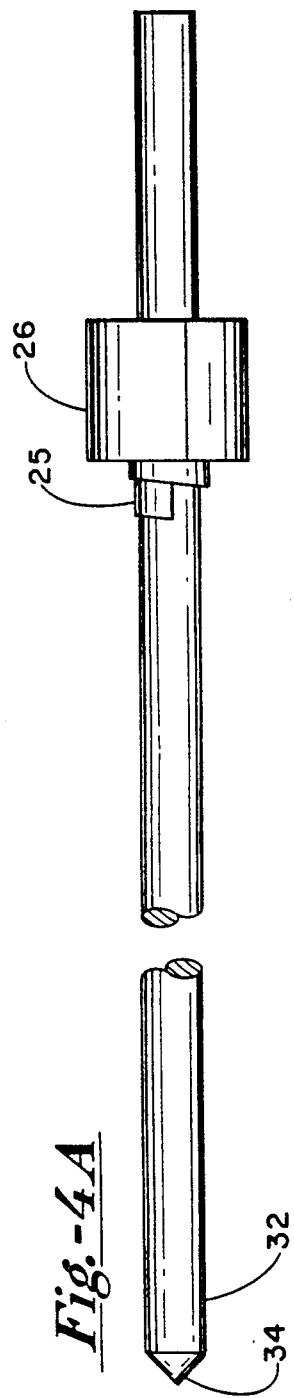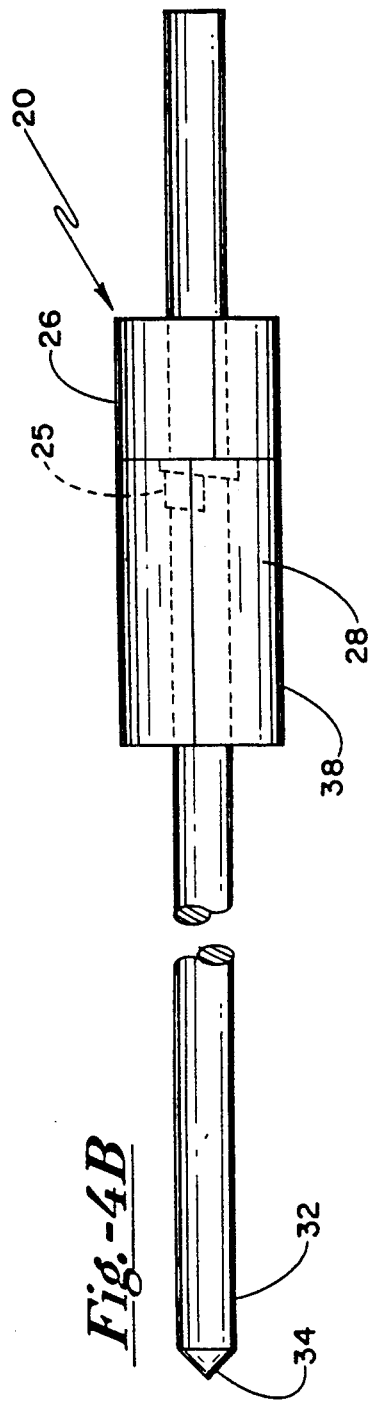

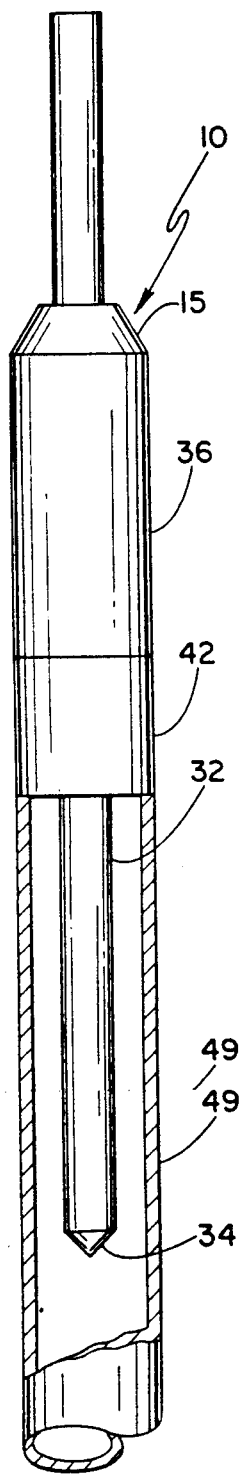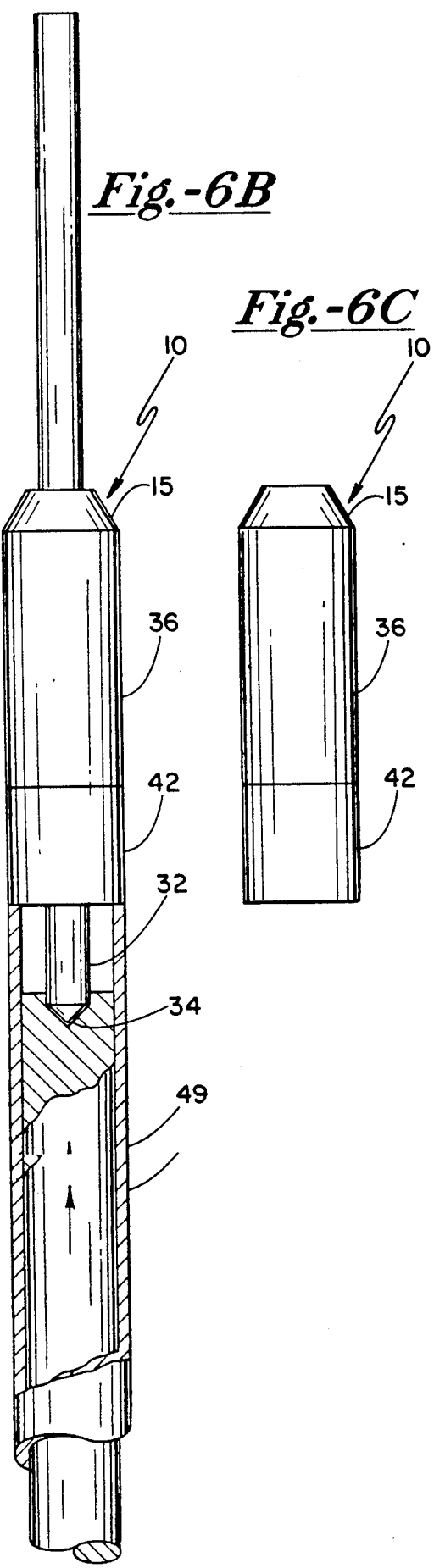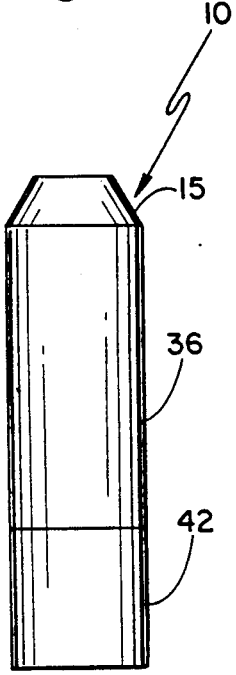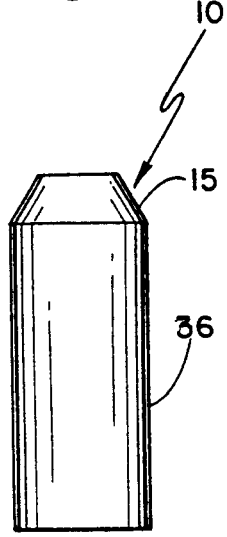
*Fig.-6A*  *Fig.-6B*  *Fig.-6C*  *Fig.-6D*

HEMOSTATIC PLUG

BACKGROUND OF THE INVENTION

1. Field of the Invention

This invention relates generally to a method of making a hemostatic plug for placement at a site where hemostatic treatment is indicated such as a puncture wound, and in particular to a method for making the plug wherein the plug comprises a rolled sheet of a hemostatic material which tends to unfurl after placement in a wound cavity and thereby fill the wound cavity.

2. Discussion of the Prior Art

Hemostatic treatment can be indicated at a variety of sites where a patient exhibits bleeding. An example of such a site occurs when performing angioplasty, angiography, or other procedures requiring establishment of an entry into a blood vessel of a patient. After such a procedure, it is necessary to effectuate closure of the resulting puncture wound upon withdrawal of instrumentation employed in performing the medical procedure and in maintaining the puncture entry of the blood vessel. Traditional approaches employed to promote wound closure include hand pressure, pressure bandages, clamps and the like to maintain pressure over the region of the wound for a time sufficient to stop bleeding. U.S. Pat. Nos 4,852,568, 4,890,612, 4,838,280 and 4,936,835 disclose the use of a plug made of a solid mass of a hemostatic material for placement at the wound site. Co-pending application Ser. No. 912,921, filed Jul. 13, 1992, and assigned to the same assignee as the present invention and incorporated herein by reference, teaches a hemostatic plug having an opening throughout its longitudinal axis so that it can be accommodated and placed in coaxial relationship with a novel implant introducer device described and claimed in that application. Except for the opening along its longitudinal axis, the plug described in the copending application is constructed from a solid mass of hemostatic material.

Because speed is of the essence in closing a puncture wound to thereby stop bleeding, it is advantageous to have hemostatic material whose configurations and characteristics cause rapid and effective wound cavity occupation and blood flow stoppage.

It is therefore a primary object of the present invention to provide a method of making a hemostatic plug which rapidly fills a wound cavity and which provides advantageous surface area presentment to promote hemostasis.

Another object of the present invention is to provide a method of making a hemostatic plug constructed from a sheet of a hemostatic material rolled upon a cylindrical forming tool whereby the plug subsequently unfurls in a wound cavity to thereby fill the cavity and increase cavity pressure while presenting advantageous surface area for fluid absorption and blood flow cessation.

Still another object of the present invention is to provide a method of making a hemostatic plug from one sheet of single density hemostatic material or from two separate sheets of hemostatic material having two different densities.

These and other objects of the present invention will become apparent throughout the description which now follows.

SUMMARY OF THE INVENTION

The present invention is a method of making a hemostatic plug for placement at a site where hemostatic treatment is indicated. The method comprises rolling a sheet of hemostatic material a plurality of turns on a generally-cylindrical forming tool to thereby produce a rolled hemostatic plug having an opening therethrough along its longitudinal axis. The plug so produced can be, for example, a single density or a dual density, with the former comprising a rolled sheet of single density hemostatic material and the latter comprising two joined rolled sheets of different densities in tandem to each other. It is to be understood that, throughout this application, the term "single density plug" refers to the density characteristics of the initial sheet of hemostatic material used to construct the plug and that the term "dual density plug" refers to the density characteristics of each of two sheets of hemostatic material which initially respectively possess two different densities. Because the plugs produced according to the present invention are rolled sheets rather than a solid mass of hemostatic material, they unfurl when situated in a wound cavity and subjected to blood and tissue fluid emitting from the wound. The plugs thereby provide increased surface area and correspondingly more rapid efficacy within the wound cavity to promote blood flow cessation and healing.

A typical site where hemostatic treatment is indicated and for which a plug produced according to the present invention can be employed is a puncture wound resulting from an angioplasty or angiography procedure. Specifically, the wound includes an entry penetration of an artery and a tissue channel leading from the surface of a patient's skin to the site of artery penetration. Thus, the plug must be sized to fit within the tissue channel so that its distal end is adjacent to the artery penetration site. A care provider can choose, for example, a low density plug, a preferred medium density plug, a high density plug, or a dual density plug. A low density plug has a greater absorption rate, yet less potential compression force. Conversely, the high density plug typically has a lower absorption rate and a higher potential compression force. Where typically both a relatively normal absorption rate and pressure application are desired, a care provider will employ a medium density plug which provides characteristics of favorable absorption as well as pressure. Also available according to the present invention is a dual density plug whose construction provides a lower density distal portion for positioning at the artery penetration site and a higher density proximal portion for positioning in the tissue channel. The distal portion absorbs blood from the penetration site while providing hemostatic activity, while the proximal portion provides higher density and pressure in the tissue channel as well as hemostatic activity.

The preferred method of making the preferred single density plug is accomplished by rolling a sheet of hemostatic material on a generally cylindrical forming tool, preferably followed by longitudinal compression of the rolled sheet while on the forming pin, to form the plug. A dual density plug is formed by first rolling a sheet of lower density hemostatic material on the forming tool so that a wedge portion of sheet material extends proximally from the rolled sheet at the rolled sheet's longitudinal axis. Thereafter, a sheet of higher density hemostatic material is rolled on the forming tool and positioned so that the higher density sheet overlaps the wedge portion of the lower density sheet. The resulting composite roll preferably is then longitudinally compressed while on the forming tool to form the plug. Employment of the forming tool in the manufacture of the plug results in an opening along the longitudinal axis of the plug so that the plug can be delivered to the wound site on a guidewire or other cylindrical placement device.

Plugs produced according to the instant invention provide versatility in the treatment of puncture wounds as above described by providing to a wound cavity a maximized hemostatic surface area to promote hemostasis and wound healing. Both the penetration site of the artery and the tissue channel leading to the artery are thereby effectively treated through fluid and blood absorption, hemostatic action, and pressure application to aid in the healing process of the wound.

BRIEF DESCRIPTION OF THE DRAWINGS

FIG. 3 is an elevation view of a single density sheet of hemostatic material rolled on a forming pin to thereafter form the plug of FIG. 1;

FIG. 4a is an elevation view of a lower density sheet of hemostatic material rolled on a forming pin;

FIG. 4b is an elevation view of the rolled lower density sheet of FIG. 4a and a higher density sheet of hemostatic material rolled adjacent the lower density sheet to thereafter form the plug of FIG. 2;

FIGS. 6a-6d are side elevation views illustrating removal of the plug of FIG. 1 from the forming pin.

DETAILED DESCRIPTION OF THE PREFERRED EMBODIMENT

Figure 1:
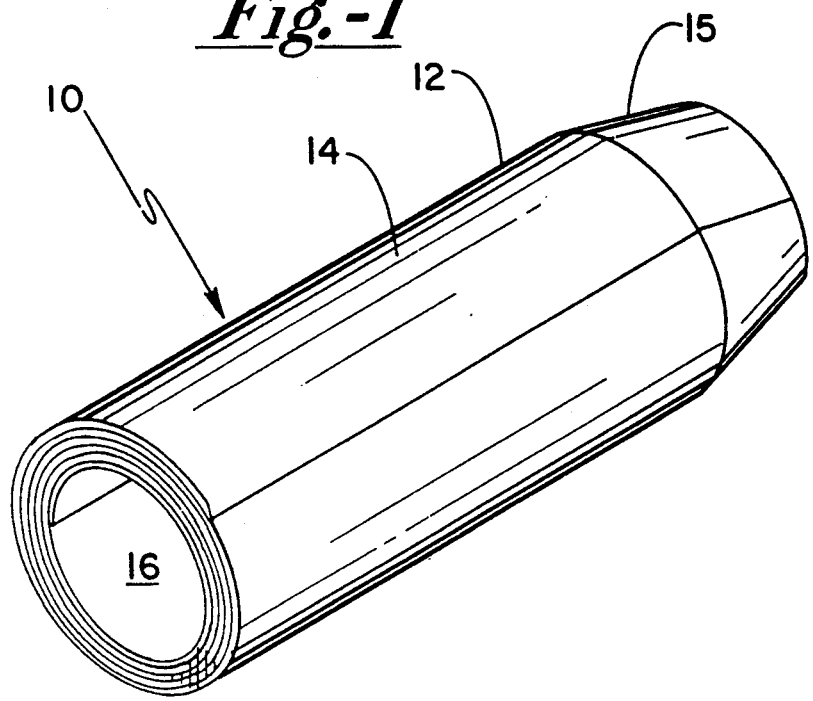
FIG. 1 is an enlarged perspective view of a single density hemostatic plug for closing a puncture wound.

Referring to FIG. 1, a single density hemostatic plug 10 is shown. Constructed according to the present invention, the plug 10 is a compressed rolled sheet 12 of hemostatic material 14 sized to fit the dimensions of a puncture wound. The distal end 15 of the plug 10 is tapered at about 10 degrees to thereby provide both better movement through a wound channel and an improved tactile sense when the distal end 15 reaches the artery site. Taper magnitude preferably can be from about 10 degrees to about 45 degrees. Thickness of the compressed sheet 12 is preferably between about 0.010 and 0.020 inch, and most preferably between about 0.014 and about 0.016 inch, while the diameter of the plug 10 can be chosen as required by the number of times the sheet 12 is rolled upon itself. Typical diameter choices of plugs 10 are 5–7 French and 7–9 French, but, of course, can be manufactured as desired. In the preferred single density plug 10, here shown, the plug 10 is constructed of collagen and has a diameter of 5–7 French. The characteristics of the sheet 12 prior to plug construction are as follows: density—about 0.0373 grams per square inch; weight—about 0.06 gram; width—about 0.70 inch; and length—about 2.30 inch. The collagen here employed is that as is currently available from Vitaphore Corporation, Menlo Park, Calif., under the name "Collastat." As is recognized by the skilled artisan, however, any hemostatic sheet material can be employed to achieve the objectives here described. Non-limiting additional examples of such materials known in the art to have hemostatic activity include hemostatic gelatin, modified polyglycolic acid-based material, and thrombin. Thus, any hemostatic material can be employed in practicing the present invention so long as that material is capable of being formed into a thin sheet which then can be rolled on a generally cylindrical forming tool. An opening 16 extends substantially along the longitudinal axis of the plug 10 for its entirety. The opening 16 accommodates a guidewire (not shown) or other cylindrical placement device for positioning the plug 10 at a wound site.

Figure 2:
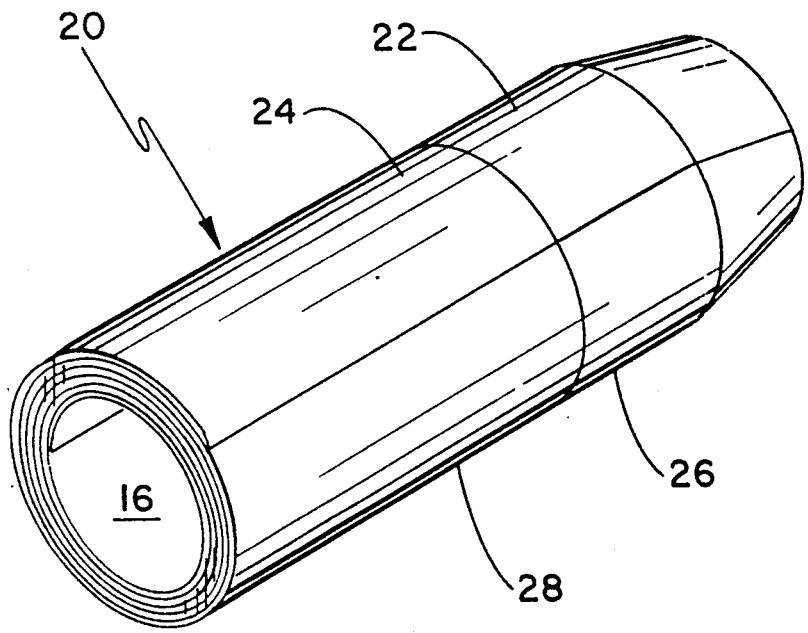
FIG. 2 is an enlarged perspective view of a dual density hemostatic plug.

FIG. 2 illustrates a dual density hemostatic plug 20 made according to the present invention wherein a first portion 22 thereof has a first density and a second portion 24 thereof has a second density which is greater than that of the first portion 22. Instead of being constructed of a single rolled sheet of hemostatic material, the plug 20 is constructed of a first lower density sheet 26 and a second higher density sheet 28. A small portion of the higher density second portion 24 overlaps a single thickness of a wedge portion 25 of the lower density sheet 26 as shown in FIGS. 4a and 4b. The hemostatic material of both of the sheets 26 and 28 is the same as that employed in the single density plug 10 of FIG. 1. Sheet dimensional characteristics of the dual density plug 20 are, of course, different from each other. For example, and assuming a plug total weight of about 0.06 gram is desired and a plug 20 is one-third lower density and two-thirds higher density, the lower density first collagen sheet 26 can have a density of about 0.0373 grams per square inch, a weight of about 0.02 gram, a width of about 0.22 inch, and a length of about 2.40 inch, while the higher density second collagen sheet 28 has density of about 0.1075 grams per square inch, a weight of about 0.04 gram, a width of about 0.50 inch, and a length of about 0.74 inch. As with the plug of FIG. 1, an opening 16 extends longitudinally through the plug 20. Of course, weights and physical dimensions can be chosen as would be recognized by a skilled artisan to produce a plug having properties as desired by the user. As with the plug 10, non-limiting examples of hemostatic material in addition to collagen include hemostatic gelatin, modified polyglycolic acid-based material and thrombin. In the dual density plug the two components thereof exhibiting different densities can be constructed of the same or different hemostatic materials.

The following procedure details the methodology employed in constructing the single density hemostatic plug 10 as shown in FIG. 1, and a dual density plug 20 as shown in FIG. 2. In particular, with respect to the single density plug 10, a piece of hemostatic material approximately 2.5 inch by 2.0 inch is compressed as with a roller mill to a thickness of about 0.014 to 0.016 inch. The weight ($W_b$) of the resulting thin piece is then determined and its density ($D_b$) in grams per square inch is determined according to the formula $D_b = W_b/A_b$, where $A_b$ is the surface area of the thin piece. Preferred plug depth, ($S_w$), which is actually the width of a sheet to be rolled to form the plug, of the plug 10 is from about 0.65 inch to about 0.75 inch, while total weight ($W_s$) is preferred to be about 0.06 gram. Sheet length ($S_l$) is then determined according to the formula $S_l = W_s/(D_b \times S_w)$. In the preferred embodiment the hemostatic material has a density of about 0.0373 grams per square inch, a width ($S_w$) of about 0.70 inch and a length of about 2.30 inch. The sheet should be cut immediately after being compressed by the aforementioned mill rolling since thickness can be regained over time. Cutting should be accomplished with a sheering device such as scissors since straight edge or blade cutting does not result in a clean cut.

Formation of the dual density plug 20 is accomplished by using a combination of a lower density hemostatic sheet 26 and a higher density hemostatic sheet 28 in a single plug. In particular, and where the weight of the plug 20 is to be the same weight (about 0.06 grams) as that of the single density plug 10, the distal one-third of the plug 20 is formed with a lower density collagen sheet 26 having a width ($S_w$) of about 0.22 inch, a length ($S_l$) of about 2.40 inch and a density of about 0.0373 grams per square inch to provide a weight of about 0.02 gram. The proximal two-thirds of the plug 20, having a weight of about 0.04 gram, is formed from a higher density collagen sheet 28 having a width ($S_w$) of about 0.50 inch, a length ($S_l$) of about 0.74 inch and a density of about 0.1075 grams per square inch. As is evident, the lower density distal end of the plug 20 is the same as that of the single density plug 10. Combining the two sheets will be described later.

A generally cylindrical forming tool, here a forming pin 32, having a uniform diameter except for a conical end 34 is used as a spool upon which the sheets are rolled. The conical end 34 of the forming pin 32 is provided so that subsequent forming tools as described later which slide on the forming pin 32 can be easily introduced. Formation of a single density plug 10 is accomplished by hand by rolling the sheet 12 tightly on the pin 32, as shown in FIG. 3, with each turn of the sheet's edges in alignment with the edges of all other turns. It is to be noted that, due to the mill rolling, one side of the sheet 12 has a satin dull finish while the other side has a shiny appearance. The sheet 12 should be rolled on the forming pin so that the shiny side is exposed. After rolling a sheet 12 on the forming pin 32, the resulting single density plug precursor 36 is smoothed as with a paddle to blend any roughened transitions.

As earlier noted, a dual density plug 20 is formed by combining a lower density sheet 26 and a higher density sheet 28, as compared to each other. This combination is accomplished by, as illustrated in FIGS. 4a and 4b, first rolling the lower density sheet 26 on the forming pin 32. In order to secure the lower density and higher density sheets together, the innermost corner only of the first roll of the lower density sheet 26 is positioned to be slightly off of the wrap line. This creates a wedge 25 of lower density material to be overlapped by the subsequently rolled higher density sheet 28. The remainder of the lower density sheet 26 is then rolled in straight alignment on the forming pin. Thereafter, the high density sheet 28 is positioned and rolled straight (edges of each turn in alignment) on the forming pin 32 so that the higher density sheet 28 overlaps the protruding wedge 25 of the lower density sheet 26. The roll direction of both the lower density sheet 26 and the higher density sheet 28 must be the same. After rolling is completed, the resulting dual density precursor plug 38 should be smoothed as necessary to blend any toughened transitions.

While the term "plug precursor" has been used above, this term is chosen merely to indicate that additional manufacturing steps can be taken as described below to achieve construction of a final preferred plug device. However, it is to be understood that the "plug precursors" described above are operational and have utility as hemostatic plugs without further modification.

All of the following optional, but preferred, construction steps are identical for both the single density plug 10 and dual density plug 20 after the sheet material has been rolled onto the forming pin. Therefore, while the following description of methodology will speak toward a single density plug, it is to be understood that the same methodology applies to construction completion of a dual density plug.

Figure 5A:
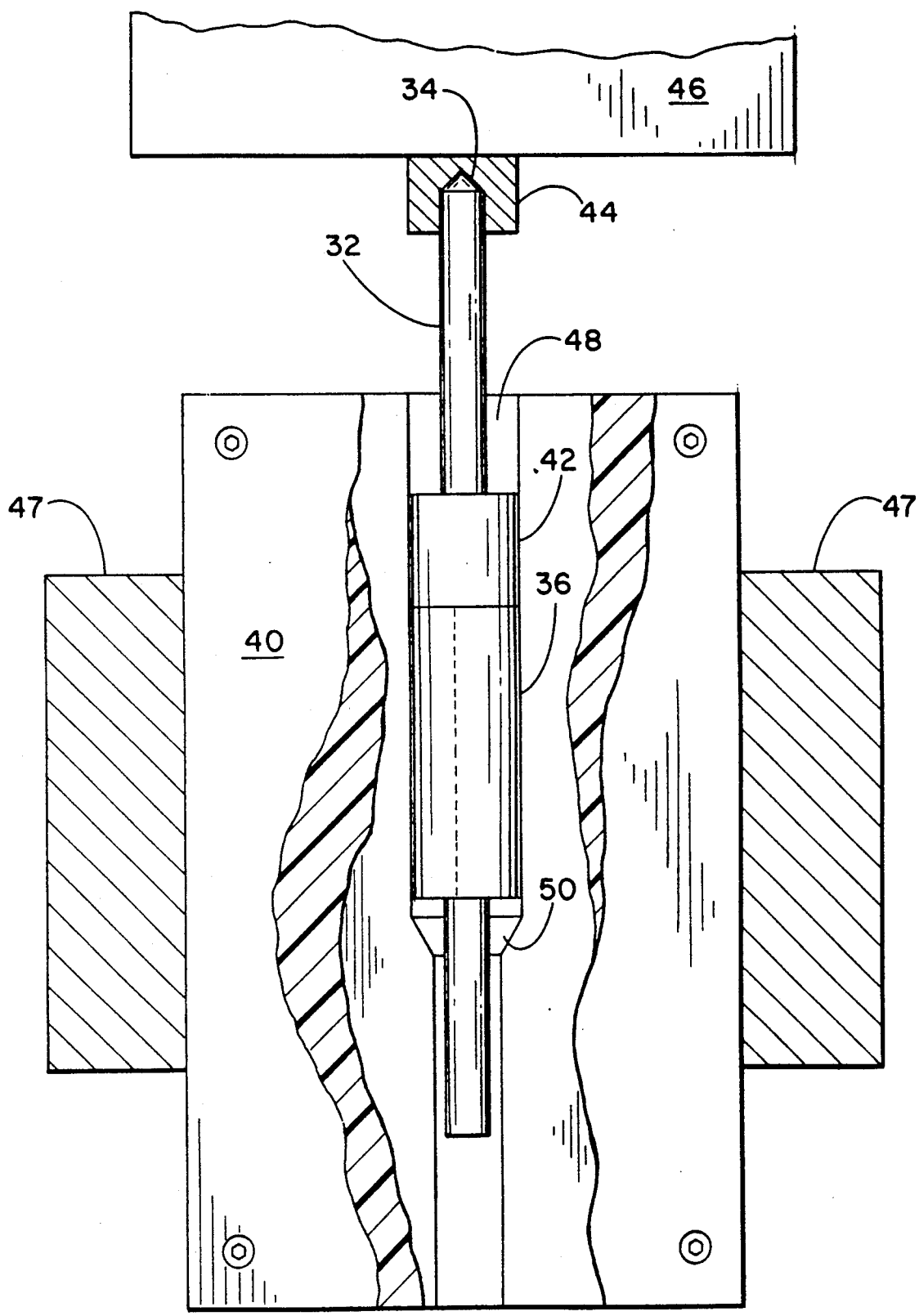
FIGS. 5a and 5b are side elevation views, partially in section, showing formation of a hemostatic plug within a forming block.
Figure 5B:
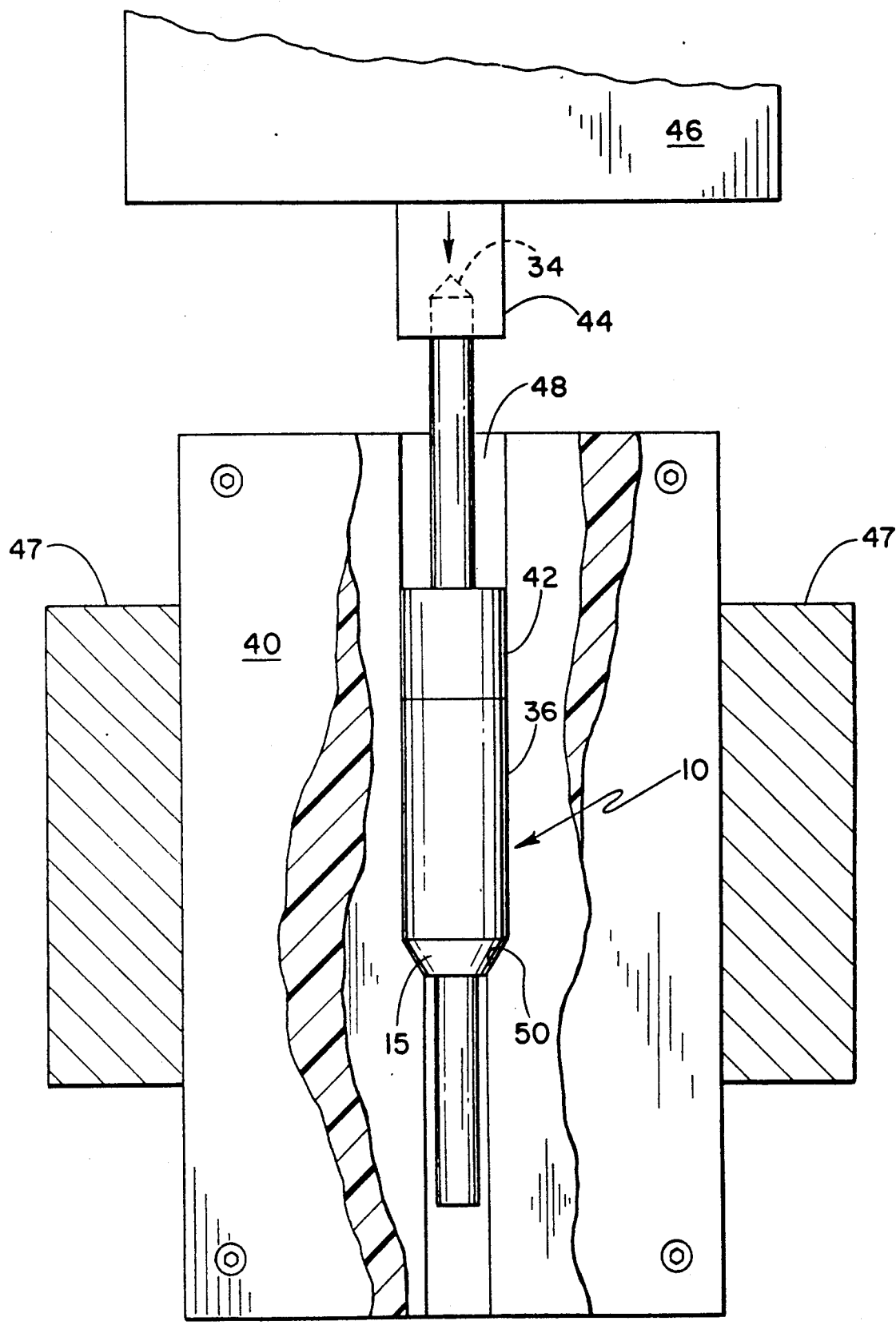

By longitudinally compressing a precursor plug as defined above, the resulting plug can longitudinally expand after placement at a wound site to a depth approximating the dimension of the precursor plug. In order to achieve this preferred longitudinal compression of the precursor plug 36 rolled on the forming pin 32 to thereby produce the hemostatic plug 10, certain forming tools are employed as illustrated in FIGS. 5a and 5b. In addition to the forming pin 32 already described, these tools include a forming block 40, a plug pusher 42, a compression tube 44, a vertical press 46 and a vise 47 to hold the block 40 in place. The forming block is two piece and has at least one cylindrical cavity 48 therein where the precursor plug 36 still rolled on the forming pin can reside. Once the precursor plug 36 is placed within the cavity, the two-piece block is assembled and mounted in the vise 47 situated in alignment with and beneath the compression tube 44 extending from a vertical press 46. The plug pusher 42 is slid onto the protruding portion of the forming pin 32 and advanced so that its distal end is juxtaposed with the end of the precursor plug situated within the block 40. The protruding portion of the forming pin 32 is aligned with the compression tube 44 which extends from the vertical press 46 so that the compression tube 44 will slide onto the forming pin 32 and into the cavity 48 of the forming block 40 when the vertical press 46 is activated. The compression tube 44 is then advanced over the forming pin 32 to contact the plug pusher 42 and is driven into the cavity 48 of the forming block 40 a depth necessary to compress the precursor plug 36 as desired to thereby form the completed hemostatic plug 10. The end 50 of the cavity 48 within the forming block 40 is shaped to provide the taper to the distal end 15 of the completed plug 10. Generally, the precursor plug 36 is compressed to about 50% of the original length to result in a length (depth) of about 1 cm, which represents a usual desired distance proximally from the site of arterial penetration. Of course, any length is attainable by varying the dimensional parameters as recognized by a skilled artisan. Thereafter, the forming block 40 is opened and the resultant hemostatic plug 10, plug pusher 42 and forming pin 32 are removed. As shown in FIGS. 6a–6d, a stripping tube 49 is then placed onto the forming pin 32 at its conical end 34 and is advanced against the plug pusher 42 to thereby push the plug pusher 42 and adjacent hemostatic plug 10 off of the forming pin 32. The plug pusher 42 then falls away and construction of the preferred hemostatic plug 10 is complete.

Figure 7:
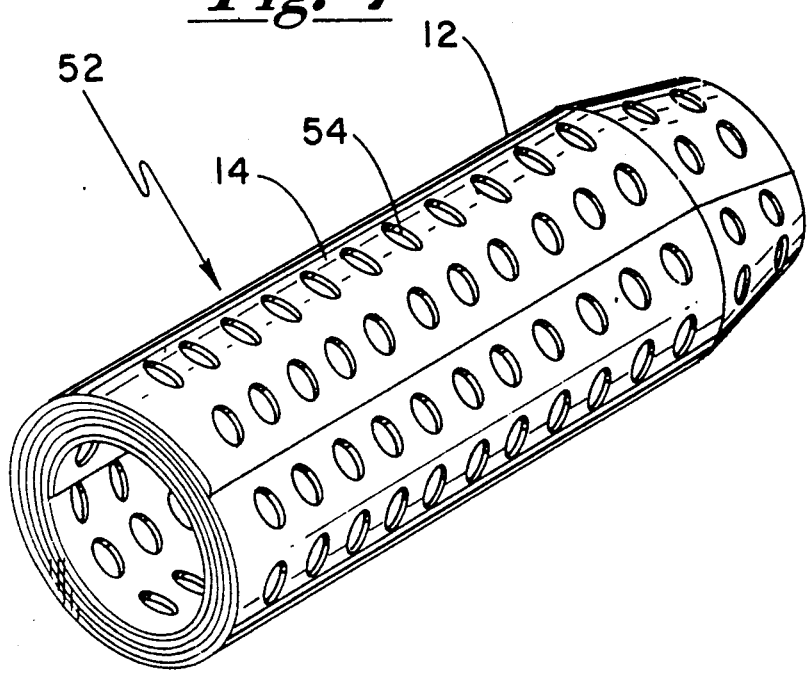
FIG. 7 is an enlarged perspective view of a single density hemostatic plug having lateral openings along its length.

FIG. 7 illustrates a third embodiment of a hemostatic plug 52 which is identical to the plug 10 of FIG. 1 except for having a plurality of holes 54 therein to thereby provide more immediate surface area availability for blood and fluid absorption. The holes 54 are placed in the plug 52 with a sharp instrument such as a pin or a stamping operation subsequent to longitudinal compression of the precursor plug as described above.

Delivery and use of a hemostatic plug is fully described in the incorporated, commonly assigned patent application referenced. Briefly, in relation to each of the plugs of the present invention, such plug is delivered to the site of the blood vessel puncture by way of a coaxial delivery tool which reaches the puncture site on a guidewire already in place. Upon reaching the wound site, the plug is released from the delivery tool and the tool, guidewire and any additional apparatus at the wound site are withdrawn. The rolled plug is immediately subjected to blood and tissue fluid which cause the plug to unfurl or unroll to the boundaries of the wound cavity and thereby fill the wound cavity. This rolled feature of the plug provides two major benefits: it causes rapid occupation of the wound cavity upon unrolling, and it presents a large surface area after such unrolling for blood and tissue fluid contact. The former benefit results in quick fluid absorption and resultant pressure against the wound. The latter benefit, large surface area, results in more rapid hemostasis to thereby aid in blood flow cessation. When a dual density plug 20 is used, the lower density portion 22 of the plug 20 is adjacent the blood vessel puncture, while the higher density portion 24 is proximal within the wound cavity or tissue channel between the blood vessel and skin. Tissue fluid and blood from the tissue channel act to unroll and swell this higher density portion 24 to thereafter produce inner wound pressure and greater resistance because of higher density to fluid and blood flow from the wound site.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A hemostatic plug for placement in a wound site where hemostatic treatment is indicated, the plug comprising at least one sheet of a hemostatic material of a predetermined length dimension, said sheet being rolled upon itself a plurality of times to create a tubular structure, said tubular structure being of a compressed length less than said predetermined length dimension, and having an opening along a longitudinal axis over its entire compressed length.

2. A hemostatic plug as claimed in claim 1 wherein one end of said tubular structure is tapered at an angle of from about 10 degrees to about 45 degrees.

3. A hemostatic plug as claimed in claim 1 wherein the hemostatic material is chosen from the group consisting of collagen, hemostatic gelatin, modified polyglycolic acid-based material and thrombin.

4. A hemostatic plug as claimed in claim 3 wherein the hemostatic material is collagen.

5. A hemostatic plug as claimed in claim 1 wherein the plug is constructed of a single sheet of hemostatic material having a single density.

6. A hemostatic plug as claimed in claim 5 wherein the hemostatic material is collagen having a density from about 0.032 to about 0.042 gram per square inch.

7. A hemostatic plug as claimed in claim 6 wherein the collagen has a density from about 0.037 to about 0.038 gram per square inch.

8. A hemostatic plug for placement at a site where hemostatic treatment is indicated, the plug comprising a first rolled sheet of hemostatic material rolled upon itself a plurality of times and having a first density, and a second rolled sheet of hemostatic material rolled upon itself a plurality of times and having a second density, with said first and second rolled sheets disposed in tandem to each other and having an opening along a longitudinal axis for its entirety.

9. A hemostatic plug as claimed in claim 8 wherein the hemostatic material of the first rolled sheet and the second rolled sheet is collagen.

10. A hemostatic plug as claimed in claim 9 wherein the density of the collagen of the first rolled sheet is from about 0.032 to about 0.042 gram per square inch, and the density of the collagen of the second rolled sheet is from about 0.095 to about 0.115 gram per square inch.

11. A hemostatic plug as claimed in claim 10 wherein the density of the collagen of the first rolled sheet is from about 0.037 to about 0.038 gram per square inch, and the density of the second rolled sheet is from about 0.105 to about 0.110 gram per square inch.

* * * * *